(12) United States Patent
Wahrburg

(10) Patent No.: US 6,228,089 B1
(45) Date of Patent: May 8, 2001

(54) DEVICE FOR POSITIONING AND GUIDING A SURGICAL INSTRUMENT DURING ORTHOPAEDIC INTERVENTIONS

(75) Inventor: Jürgen Wahrburg, Marienheide (DE)

(73) Assignee: Depuy International Limited, Leeds (GB)

( * ) Notice: Subject to any disclaimer, the term of this patent is extended or adjusted under 35 U.S.C. 154(b) by 0 days.

(21) Appl. No.: 09/331,561
(22) PCT Filed: Dec. 19, 1997
(86) PCT No.: PCT/EP97/07186
§ 371 Date: Jul. 1, 1999
§ 102(e) Date: Jul. 1, 1999
(87) PCT Pub. No.: WO98/27887
PCT Pub. Date: Jul. 2, 1998

(51) Int. Cl.$^7$ ............................. A61F 5/00; A61F 19/00
(52) U.S. Cl. ............................. 606/86; 606/130
(58) Field of Search ............................. 606/130, 53, 86; 600/426, 427, 429; 901/46, 50, 15, 4

(56) References Cited

U.S. PATENT DOCUMENTS

| | | | |
|---|---|---|---|
| 5,086,401 | * | 2/1992 | Glassman et al. . |
| 5,178,164 | * | 1/1993 | Allen ........................... 606/97 X |
| 5,211,164 | * | 5/1993 | Allen ........................... 606/130 X |
| 5,343,391 | * | 8/1994 | Mushablac .................. 433/72 X |
| 5,657,429 | * | 8/1997 | Wang et al. . |
| 5,695,500 | * | 12/1997 | Taylor et al. ................... 606/130 |
| 5,776,136 | * | 7/1998 | Sahay et al. ................... 606/79 |
| 5,806,518 | * | 9/1998 | Mittelstadt . |
| 5,824,085 | * | 10/1998 | Sahay et al. ................... 606/86 X |
| 5,950,629 | * | 9/1999 | Taylor et al. . |

FOREIGN PATENT DOCUMENTS

| | | |
|---|---|---|
| 196 01 857 A1 | 8/1996 | (DE) . |
| 0 566 103 A2 | 11/1991 | (EP) . |
| 0 469 966 A1 | 2/1992 | (EP) . |

* cited by examiner

Primary Examiner—Jeffrey A. Smith
(74) Attorney, Agent, or Firm—Herbert Dubno

(57) ABSTRACT

The invention relates to a device for positioning and guiding a surgical instrument during orthopaedic interventions, comprising an industrial robot which has a program-controlled robot arm (1) with several articulated joints and a mounting plate (2) at the end of said arm, an instrument (3) for the orthopaedic intervention attached to the mounting plate (2) and a program control with computer. Sensors for detecting the position of the joints in an instrument-coordinating system defined in the program control are situated in the joints of the robot arm (1). According to the invention, a manually guided sensor device, for example in the form of a sensor arm (4) with multiple joints, is used for the three-dimensional measurement of an object by the instrument-coordinating system of the industrial robot. Using the sensor device (4), and with a previously adopted basic position of the robot arm (1) specified by the program control, reference points can be detected on the bone of the patient. From the coordinates of the reference points related to the instrument-coordinating system the computer calculates a working position, which the robot arm (1) subsequently assumes during the surgical intervention.

11 Claims, 4 Drawing Sheets

DEVICE FOR POSITIONING AND GUIDING A SURGICAL INSTRUMENT DURING ORTHOPAEDIC INTERVENTIONS

CROSS REFERENCE TO RELATED APPLICATIONS

This application is a national stage of PCT/EP97/07186 filed Dec. 19, 1997 and based upon German national application 19653966.8 of Dec. 21, 1996 under the International Convention.

FIELD OF THE INVENTION

The present invention relates to a device for positioning and guidance of a surgical instrument during orthopaedic operations, with an industrial robot having a program-controlled multi-jointed robot arm with a mounting plate on its end, an instrument for the surgical procedure held on the mounting plate, and a program control system with computer, whereby sensors are arranged in the joints of the robot arm to determine the joint positions in an instrument coordinate system in the program control system and whereby the robot arm can be moved by means of the program control system to a working position for the surgical procedure.

BACKGROUND OF THE INVENTION

A device with the features described above is known from the Jul. 29, 1994 issue of VDI Nachrichten and is used in hip operations. Before the operation, three screws are initially implanted into the patient's knee and the thigh bone. The screws have a slight indentation into which fits the head of a feeler arranged at the end of a robot arm. A computer tomograph also carried out before the operation provides necessary patient data for the program control system. During the surgical procedure, the patient's thigh is clamped in a sterile holder arm that is rigidly attached to the foot of the industrial robot. A measuring arm placed on the bone records any positional changes. Firstly, the surgeon leads the robot arm with the feeler at its end to the reference points given by the indentations in the screws, the coordinates of which are compared with the data from the tomograph. From the data, the computer then determines the working position of the robot arm for the surgical procedure. Once the working position has been determined, the feeler is replaced by an instrument and the femur shaft is milled using appropriate feed movements of the robot arm under program control. Next, the surgeon can insert a previously selected prosthesis.

The application of the known device requires extensive preoperative planning and use of computer tomography, which are not only expensive, but also prolong the operation time to an overall extent that is problematic. Also unfavorable is the fact that the surgeon has no possibility of exerting an influence on the program-controlled course of the operation. In the event of positional changes of the bone and/or non-compliance with predetermined tolerances, the device immediately interrupts its work for safety reasons.

OBJECT OF THE INVENTION

The object of the invention is to provide a device of the type described at the outset, which is deployable intraoperatively and so designed that the surgeon can exercise an influence on the operation.

SUMMARY OF THE INVENTION

According to the invention the object is achieved in that a sensor arrangement manually controllable independently of the position of the robot arm is provided for three-dimensional object measurement in the instrument coordinate system of the industrial robot, such that, by means of the sensor arrangement, using a previously-assumed home position of the robot arm prescribed by the program control system, reference points on the patient's bone can be sensed and the computer determines the working position of the robot arm from the coordinates of the reference points related to the instrument coordinate system. It is taken that the working position of the robot arm can also include a sequence of robot arm positions, which must be visited in order to guide and position optimally the instrument arranged on the mounting plate for the execution of the surgical procedure. Independently of the technical implementation of the sensor arrangement, it is of fundamental significance to the invention that through a coupling of the sensor arrangement and the robot arm, which can be realized in differing ways explained in greater detail below, the coordinates of the reference points in the instrument coordinate system of the industrial robot are determined, this being defined in the program control system.

The sensor arrangement allows a sufficient number of clearly identifiable reference points on the patient to be determined for the calculation of the working position of the robot arm. During recording of these reference points, the robot arm remains stationary in the previously assumed known home position. Using the coordinates of the home position and the coordinates of the reference points, the working position that the robot arm subsequently assumes during the surgical procedure can be calculated exactly. Depending on the type of surgical procedure, a single working position or a sequence of working positions is determined. The device according to the invention permits intraoperative application. Preoperative planning on the basis, for example, of X-ray photographs or computer tomographs is not required in principle. Furthermore, the program control system can be set up so that, during the operation on bones that are exposed during the procedure, the surgeon records further characteristic points with the aid of the sensor arrangement, which are then processed for correction of the working position of the robot arm and/or to determine a sequence of working positions which the robot arm assumes one after the other as the operation proceeds.

According to the invention, it is possible to employ sensor arrangements based on various measuring principles. One embodiment consists of a multi-jointed manually moveable sensor arm connected to the mounting plate of the robot arm. The coupling to the instrument coordinate system of the robot is achieved in this case through a rigid mechanical connection, so that the fixing of the sensor arm on the mounting plate must take place precisely at an exactly defined position. The sensor arm has joints with sensors to detect the joint positions. By manual guidance of the sensor arm at a predetermined and previously assumed home position of the robot arm, reference points on the patient's bone can be sensed, the coordinates of which are passed to the computer. From these coordinates, the computer determines the working position of the robot arm. A sensor arm with six joints is preferable.

Multi-jointed sensor arms having sensors to determine the joint positions are already known. These are passive, exclusively manually steerable measuring instruments, which are used, within the scope of known techniques, as transportable devices for measuring workpieces. The invention starts with the recognition that the attachment of a multi-jointed sensor arm to the end of a program-controlled active robot arm brings significant advantages that can be utilized in surgical procedures. Of fundamental significance to the invention is the fact that the sensor arm arranged on the mounting plate is not replaced by instruments, but is available to the surgeon throughout the entire surgical procedure.

A further embodiment of the invention provides for the sensor arrangement consisting of a multi-jointed sensor arm connected to the computer, the arm being spatially so arranged that both the patient's bone to be sensed and the mounting plate of the robot arm placed in a home position are within the working space measurable with the sensor arm, such that with the aid of the sensor arm, at least one reference point on the mounting plate can be sensed so that, by means of the sensor arm, both the position and orientation of the mounting plate and the reference points sensed on the patient's bone are determined in a fixed three-dimensional coordinate system and such that the computer transforms the spatial coordinates found into the coordinates of the instrument coordinate system. Multiple points may be provided on the mounting plate, the positions of which are exactly defined and have been determined in relation to the instrument coordinate system. Another possibility consists in moving the robot arm not only to one, but sequentially to several, and at least three, home positions. At each of these home positions, in each case only one point defined on the mounting plate is sensed with the sensor arm. In the spatial coordinate system of the sensor arrangement, this point then has different coordinates for each home position of the robot arm. Given these coordinates, the subsequently sensed spatial coordinates of the reference points on the bone can be transformed into the instrument coordinate system.

A further possibility for implementation of the sensor arrangement provides for use of a three-dimensional locating system which locates objects through the interaction of transmitter/receiver elements. Systems of this type are known in principle and can be based on optical, inductive or ultrasonic processes. According to the invention, the sensor arrangement in this case consists of a measuring arrangement with remote data transmission having a stationary receiver, a sensing probe with a first transmitter, and a second transmitter arranged on the mounting plate, such that the transmitters have multiple signal generators in a rigidly defined spatial arrangement which emit positioning signals that are received by the receiver, such that the position and orientation of the sensing probe and of the mounting plate in a spatially fixed three-dimensional coordinate system are determined from the positioning signals and such that the spatial coordinates found for the sensing probe and mounting plate can be passed to the computer, which transforms the spatial coordinates of the sensing probe into the coordinates of the instrument coordinate system.

Finally, within the scope of the invention, it is possible to employ a measuring arrangement with remote data transmission as a sensor arrangement having a stationary receiver and a sensing probe with a transmitter, such that the transmitter has several signal generators in a rigidly defined spatial arrangement which emit positioning signals that are received by the receiver, such that, with the aid of the sensing probe, at least one reference point on the mounting plate of the robot arm moved into a home position can be sensed, such that both the position and orientation of the mounting plate and of the reference points sensed on the patient's bone are determined in a spatially fixed three-dimensional coordinate system by means of the sensing probe, and such that the computer transforms the spatial coordinates determined into the coordinates of the instrument coordinate system.

According to the invention the computer develops an executable robot program from the coordinates of the reference points input with the sensor arm or the locating system, which is transferred to the program control system, such that the bone processing is undertaken under program control through a movement of the robot arm. According to a preferred embodiment of the invention, however, the instrument for the surgical procedure is guided on a carriage also affixed to the mounting plate, and is movable axially. With this embodiment of the invention, the feed movement of the surgical instrument can be carried out by the surgeon manually or with a motorized feed drive independently of the movement of the robot arm, once the surgical instrument has been placed by the device according to the invention in an optimum position and optimum orientation for the operation. This embodiment of the invention permits short operation times, such that the cuts to be performed can nevertheless be carried out very precisely, because the instrument is optimally held and guided by the device according to the invention.

The device can have an additional monitoring arrangement to determine the spatial position of the patient during the operation. The technical configuration of this monitoring arrangement is dependent on the locating system used. In the embodiment with a sensor arm, a camera is employed which detects the position of marking pegs that have been inserted into the relevant bone before the surgical procedure and the coordinates of which are sensed with the aid of the sensor arm when setting up the working position of the robot arm, such that positional changes of the marking pegs detected by the camera are processed in the computer and a correction of the working position of the robot arm is undertaken by the program control system. With utilization of a sensor arrangement with transmitter and receiver elements, the monitoring arrangement preferably has at least one reference peg, which can be affixed to the relevant bone of the patient before the surgical procedure and is equipped with a transmitter, such that the reference peg transmitter has several signal generators in a suitable manner, similarly to the sensing probe, which emit positioning signals that are received by the receiver. The bone can be located exactly and its position calculated precisely. In the event of the bone's position changing, an automatic positional adjustment of the robot arm and of the surgical instrument attached to the robot arm is made, this possibly requiring authorization by the surgeon.

BRIEF DESCRIPTION OF THE DRAWING

The invention is now described with reference to the accompanying drawing, in which.

SPECIFIC DESCRIPTION

The fundamental structure of the device includes an industrial robot having a multi-jointed, program-controlled robot arm with a mounting plate at its end, as well as a program control system with a computer. In the joints of the robot arm, there are sensors to detect the joint positions. The robot arm can be moved by means of the program control system to a working position for the surgical procedure.

Figure 1:
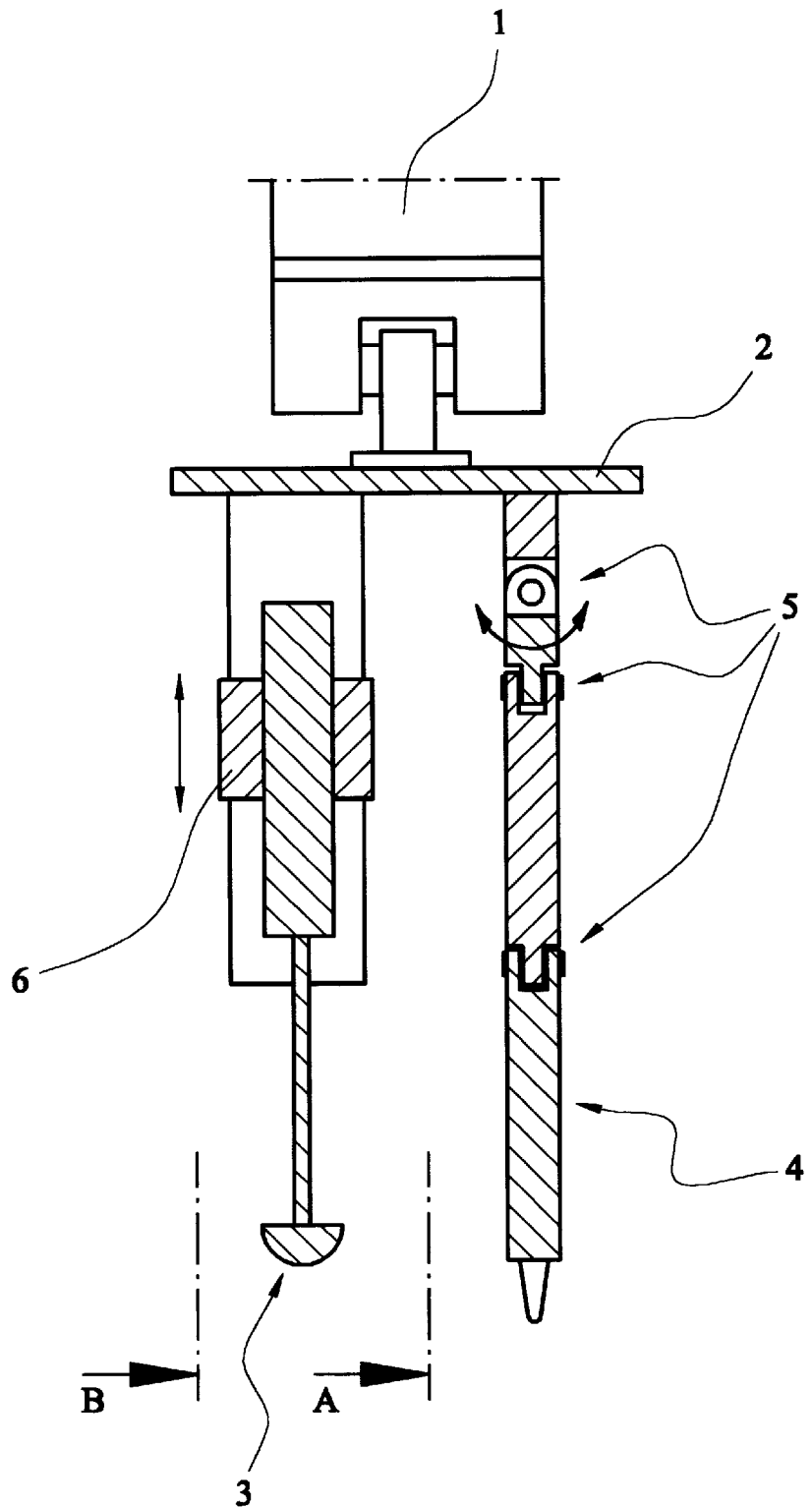
FIG. 1 shows sections of a plan view of a device for the positioning and guidance of a surgical instrument during orthopaedic operations.
Figure 2:
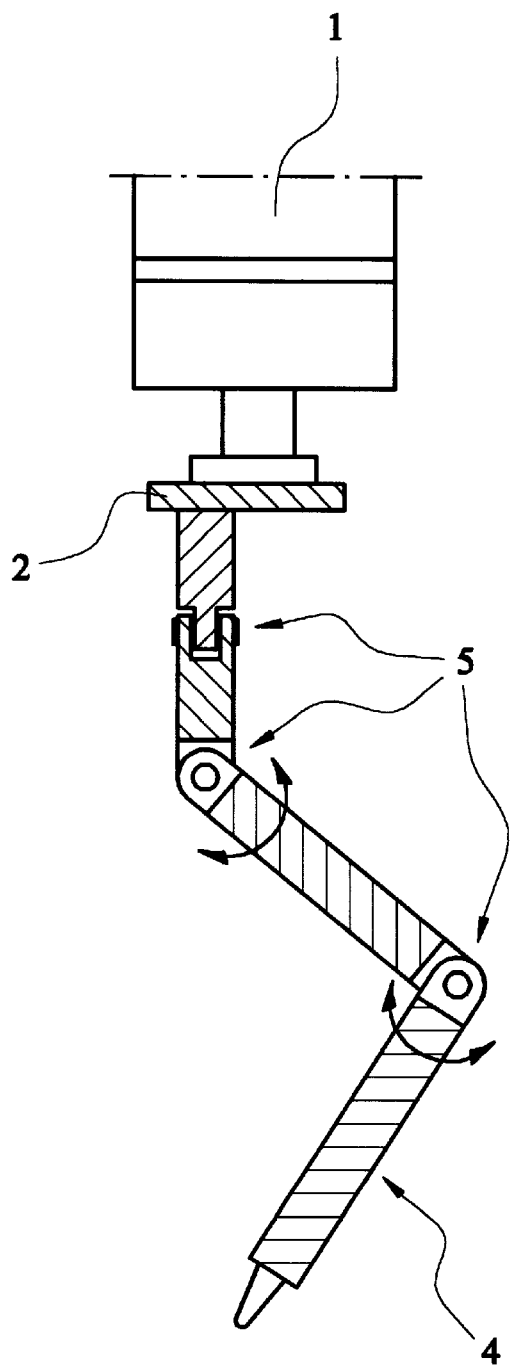
FIG. 2 shows the side elevation A in FIG. 1.
Figure 3:
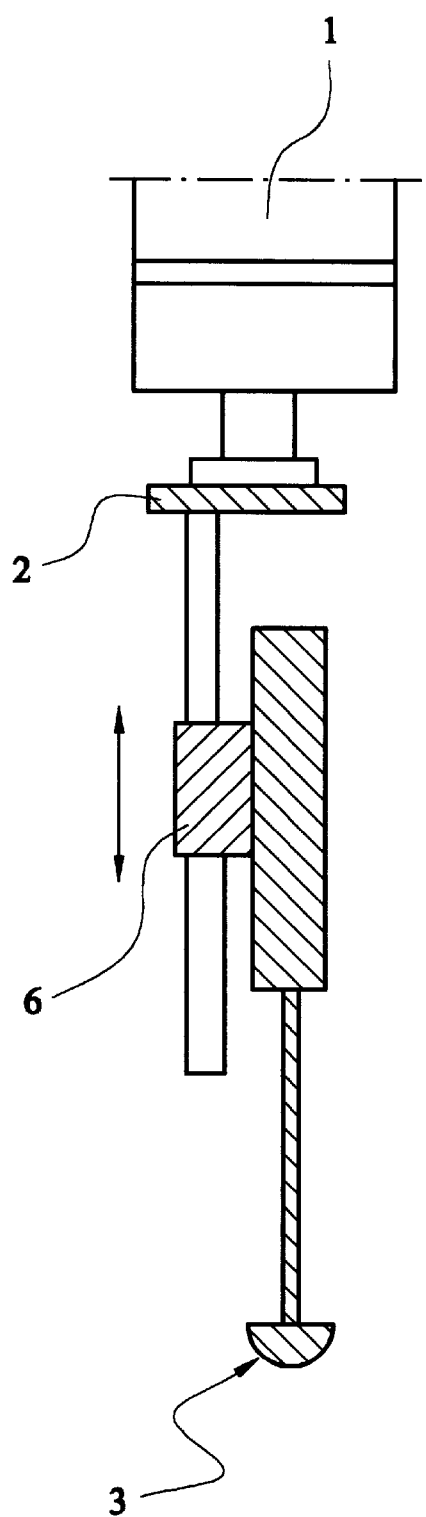
FIG. 3 shows the side elevation B in FIG. 1, and FIGS. 4 and 5 show further embodiments of the device according to the present invention schematically.

In FIGS. 1 to 3, only the free end of the robot arm 1 is shown. It has a mounting plate 2 at its end, to which are attached an instrument 3 for the orthopaedic procedure, as well as a multi-jointed, manually movable sensor arm 4. A comparison of FIGS. 1 and 2 reveals that the sensor arm 4 has at least three joints 5. Preferably there are six joints. The joints 5 have sensors, e.g. in the form of potentiometers, incremental position transducers, resolvers or the like, for determining the joint positions. With manual guidance of the sensor arm 4 at a home position of the robot arm 1 given by the program control system, reference points on the patient's bone can be sensed and their coordinates passed to the computer (not shown). From the coordinates, the computer calculates the working position that the robot arm 1 then assumes during the surgical procedure.

A comparison of FIGS. 1 and 3 reveals that the instrument 3 is movably guided axially on a carriage 6 also attached to the mounting plate 2. The carriage 6 is arranged to move orthogonally to the mounting plate 2. The feed movement of the instrument 3 can be carried out manually or with a motorized feed drive independently of the movement of the robot arm 1.

Figure 4:
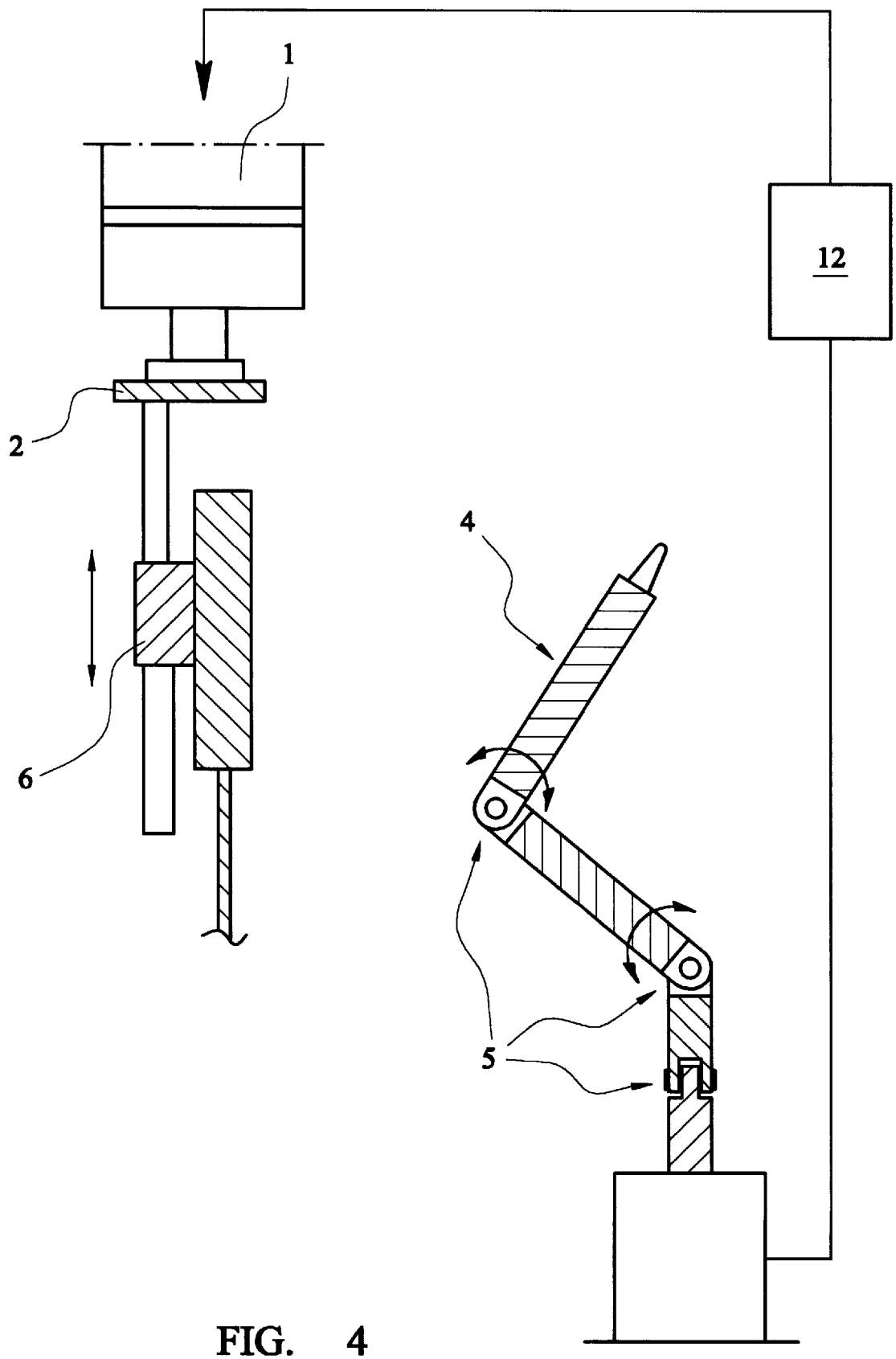

With the embodiment shown in FIG. 4, the sensor arm 4 is not attached to the mounting plate 2 of the robot arm 1, but is at a stationary location and connected to the computer 12. The position of the multi-jointed sensor arm 4 is selected so that both the bone to be sensed and the mounting plate of the robot arm 1 moved to its home position are located within the working space measurable by the sensor arm 4. With the aid of the sensor arm 4, at least one reference point on the mounting plate 2 can be sensed. By means of the sensor arm 4 both the position and the orientation of the mounting plate 2 and of the sensed reference points on the patient's bone can be determined in a spatially fixed three-dimensional coordinate system. The computer 12 transforms the spatial coordinates found into the coordinates of the instrument coordinate system. The process can be carried out in such a way that, with the aid of the sensor arm 5, several points on the mounting plate 2 are sensed, the positions of which are precisely defined in relation to the instrument coordinate system. Another procedure consists in moving the robot arm 1 not to one, but to at least three home positions in sequence. In each of these home positions, only one point of precisely known and defined position on the mounting plate 2 is sensed with the sensor arm 4. In the spatial coordinate system of the sensor arrangement, this point has different coordinates for each home position of the robot arm 1. It is also possible to derive from these coordinates a mathematical rule to define the desired coordinate transformation. The sensing of the reference points on the bone is only done after this mathematical rule has been determined.

Figure 5:
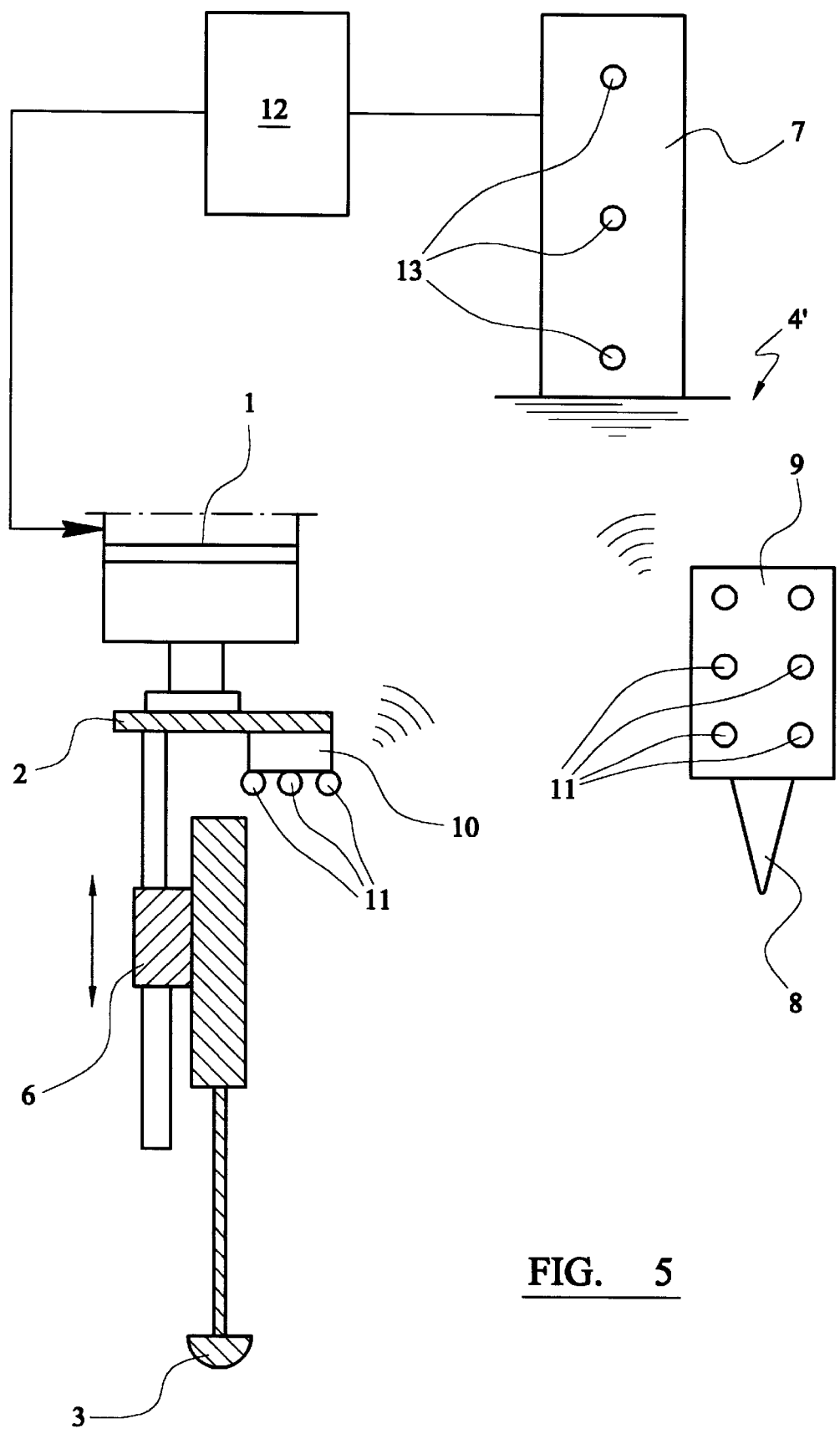

The configuration of the device according to the invention shown in FIG. 5 has a manually movable sensor arrangement for three-dimensional object measurement in the instrument coordinate system of the robot arm, consisting of a measuring arrangement 4' with remote data transfer. It comprises a stationary receiver 7, a sensing probe 8 with a first transmitter 9 and a second transmitter 10 arranged on the mounting plate 2. The transmitters 9, 10 have several signal generators 11 in a rigidly defined spatial arrangement, which emit positioning signals that are received by the receiver 7. From the positioning signals, the position and orientation of the sensing probe 8 and of the mounting plate 2 is determined in a spatially fixed three-dimensional coordinate system. The spatial coordinates of the sensing probe 8 and of the mounting plate 2 thus found can be passed to the computer 12, which transforms the spatial coordinates of the sensing probe into the coordinates of an instrument coordinate system upon which the program control system is based.

Locating systems having a measuring arrangement with remote data transfer are known in principle and can be based on optical, inductive or ultrasonic processes. The sensing probe has, for instance, a small plate with four or six infrared light-emitting diodes 11 as signal generators arranged at its corners. The light impulses transmitted from these are received by the receiver 7 situated stationary in the room, which has three separate receiving elements 13, consisting of optics and light-sensitive sensors. Making use of the precisely known geometrical arrangement of the transmitter and receiver elements 11, 13, by mathematical evaluation of all the received signals, the position and orientation of the sensing probe 8 can be calculated in the spatially fixed coordinate system. According to the invention, a suitable small plate 10 with transmitter elements 11 is also affixed to the mounting plate 2 of the robot arm 1. In this way, the positions of both the sensing probe 8 and the mounting plate 2 are found, so that the spatial coordinates of the reference points on the bone sensed with the sensing probe can be transformed through mathematical transformations into the instrument coordinate system of the industrial robot upon which the program control system is based.

What is claimed is:

1. A device for positioning and guidance of a surgical instrument during an orthopaedic operation, said device comprising:

an industrial robot having a program-controlled, multi-jointed robot arm with a mounting plate at an end of the robot arm;

an instrument for the orthopaedic operation arm on the mounting plate;

a program control system with computer connected to said robot;

a sensor arrangement for the sensing of reference points on the bones of the patient; and sensors in the joints of the robot arm for determining joint positions of the robot arm in an instrument coordinate system defined in the program control system and such that the robot arm can be moved by means of the program control system into a working position for the orthopaedic operation;

said sensor arrangement comprising a multi-jointed sensor arm affixed to the mounting plate and forming a passive manually guided measuring instrument, said sensor arm having sensors for detecting joint positions of said sensor arm, said instrument being available to the surgeon during the orthopaedic procedure such that movement of the sensor arm at a previously-assumed position of the robot arm defined by the program control system, reference points on a patient's bone can be sensed and the computer determines the working position of the robot arm for the orthopaedic operator from the positional details supplied by the sensors of the sensor arm and the positional details of the robot arm sensors measured in the instrument coordinate system.

2. The device according to claim 1, further comprising an additional monitoring arrangement to detect a spatial position of the patient during the operation with a camera detecting positions of marking pegs inserted in the bone before the operation, the coordinates of said pegs being sensed with aid of the sensor arm on setting-up of a working position of the robot arm, such that positional changes in the marking pegs detected by the camera are processed in the computer and a correction is made to the working position of the robot arm by means of the program control system.

3. The device according to claim 1 wherein the instrument is guided on a carriage affixed to the mounting plate so that it is moveable axially.

4. The device according to claim 1 wherein the carriage is arranged at a fixed angle to the mounting plate.

5. The device according to claim 1 wherein the carriage is movable orthogonally to the mounting plate.

6. Device for positioning and guidance of a surgical instrument during orthopaedic operations with an industrial robot, having a program-controlled, multi-jointed robot arm with a mounting plate at its end, an instrument for the surgical procedure held on the mounting plate, a program control system with computer, a sensor arrangement for the sensing of reference points on the bones of the patient, such that sensors are arranged in the joints of the robot arm for determining the joint positions in an instrument coordinate system defined in the program control system and such that the robot arm can be moved by means of the program control system into a working position for the surgical procedure, said sensor arrangement comprising a multi-jointed sensor arm connected to the computer and in a form of a manually-guided measuring instrument with sensors for detecting joint positions of said sensor arm and so positioned at a fixed location that both a patient's bone to be sensed and the mounting plate positioned in a home position lie within a range of the sensor arm, so that, with the aid of the sensor arm reference points on the patient's bone and at least one reference point on the mounting plate can be sensed and the computer transforms the coordinates of the reference points determined with the sensor arm in a spatially fixed three-dimensional coordinate system into coordinates of the instrument coordinate system.

7. The device according to claim 6, further comprising an additional monitoring arrangement to detect a spatial position of the patient during the operation with a camera detecting positions of marking pegs inserted in the bone before the operation, the coordinates of said pegs being sensed with aid of the sensor arm on setting-up of a working position of the robot arm, such that positional changes in the marking pegs detected by the camera are processed in the computer and a correction is made to the working position of the robot arm by means of the program control system.

8. A device for positioning and guidance of a surgical instrument during orthopaedic operations with an industrial robot, having a program-controlled, multi-jointed robot arm with a mounting plate at its end, an instrument for the surgical procedure held on the mounting plate, a program control system with computer, a sensor arrangement for the sensing of reference points on the bones of the patient, such that sensors are arranged in the joints of the robot arm for determining the joint positions in an instrument coordinate system defined in the program control system and such that the robot arm can be moved by means of the program control system into a working position for the surgical procedure, characterized in that the sensor arrangement comprising a measuring arrangement with remote data transfer, having a stationary receiver, a sensing probe with a first transmitter and a second transmitter arranged on the mounting plate, the transmitters having multiple signal generators in a rigidly defined spatial arrangement that emit positioning signals received by the receiver, the computer transforming spatial coordinates of the sensing probe determined from the positioning signals with spatial coordinates of the mounting plate also determined from the positioning signals into the coordinates of the instrument coordinate system.

9. The device according to claim 8, further comprising an additional monitoring arrangement to detect the spatial position of the patient during the operation with at least one reference peg, which can be affixed to the patient's relevant bone before the surgical procedure and equipped with a third transmitter, such that the transmitter of the reference peg which is also equipped with multiple signal generators, emits positioning signals that are received by the receiver and processed by the computer for generating a correction of the working position of the robot arm on transfer to the robot control system to track the robot to the patient.

10. A device for positioning and guidance of a surgical instrument during orthopaedic operations with an industrial robot, having a program-controlled, multi-jointed robot arm with a mounting plate at its end, an instrument for the surgical procedure held on the mounting plate, a program control system with computer, a sensor arrangement for the sensing of reference points on the bones of the patient, such that sensors are arranged in the joints of the robot arm for determining the joint positions in an instrument coordinate system defined in the program control system and such that the robot arm can be moved by means of the program control system into a working position for the surgical procedure, characterized in that the sensor arrangement comprising a measuring arrangement with remote data transfer, having a stationary receiver, a sensing probe with a transmitter, such that the transmitter has multiple signal generators in a rigidly defined spatial arrangement, that emit positioning signals received by the receiver, such that, with the aid of the sensing probe, reference points on the patient's bone and at least one reference point on the mounting plate can be sensed and the computer transforms spatial coordinates of the sensing probe determined from the positioning signals with spatial coordinates of the mounting plate, also determined from the positioning signals into the coordinates of the instrument coordinate system.

11. The device according to claim 10, further comprising an additional monitoring arrangement to detect the spatial position of the patient during the operation with at least one reference peg, which can be affixed to the patients relevant bone before the surgical procedure and equipped with a third transmitter, such that the transmitter of the reference peg which is also equipped with multiple signal generators, emits positioning signals that are received by the receiver and processed by the computer for generating a correction of the working position of the robot arm on transfer to the robot control system to track the robot to the patient.

* * * * *